United States Patent [19]

Cipolli et al.

[11] Patent Number: 5,424,345

[45] Date of Patent: Jun. 13, 1995

[54] TRIAZINYLPHOSPHONIC ACIDS AND THEIR USE IN SELF-EXTINGUISHING POLYMERIC COMPOSITIONS

[75] Inventors: Roberto Cipolli, Novara; Cristina Rossi, Rome; Roberto Oriani, Milan; Enrico Masarati, Castelnuovo Valtidone; Gilberto Nucida, San Giuliano Milanese, all of Italy

[73] Assignee: Ministero Dell 'Universita'E Della Ricerca Scientifica E Tecnologica, Rome, Italy

[21] Appl. No.: 230,842

[22] Filed: Apr. 21, 1994

Related U.S. Application Data

[62] Division of Ser. No. 990,519, Dec. 15, 1992, Pat. No. 5,350,848.

[30] Foreign Application Priority Data

Dec. 18, 1991 [IT]  Italy .............................. MI91A03400

[51] Int. Cl.$^6$ .................. C08K 5/3432; C08K 5/3492
[52] U.S. Cl. ..................................... 524/96; 524/100; 524/416
[58] Field of Search ........................ 524/96, 100, 416

[56] References Cited

U.S. PATENT DOCUMENTS

| | | | |
|---|---|---|---|
| 5,302,640 | 4/1994 | Cipolli et al. | 524/100 |
| 5,302,642 | 4/1994 | Cipolli et al. | 524/100 |
| 5,344,931 | 9/1994 | Cipolli et al. | 524/100 |

*Primary Examiner*—Paul R. Michl
*Assistant Examiner*—P. Hampton-Hightower
*Attorney, Agent, or Firm*—Oblon, Spivak, McClelland, Maier & Neustadt

[57] ABSTRACT

Triazinylphosphonic acids of general formula (I):

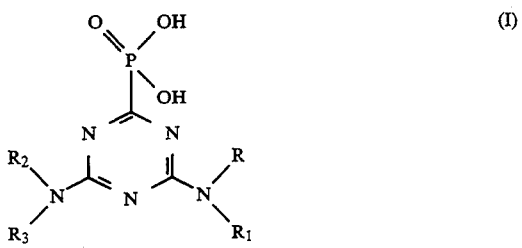

obtained by subsequent condensation reaction of a cyanuric halide with a phosphite and with amines, and then by hydrolysis reaction of the intermediate thus obtained. The compounds of general formula (I) are used in particular as flame retardant additives.

15 Claims, No Drawings

TRIAZINYLPHOSPHONIC ACIDS AND THEIR USE IN SELF-EXTINGUISHING POLYMERIC COMPOSITIONS

This application is a divisional application of Ser. No. 07/990,519, filed Dec. 15, 1992, now U.S. Pat. No. 5,350,848.

BACKGROUND OF THE INVENTION

1. Field of the Invention

This invention relates to triazinylphosphonic acids. More specifically, the invention relates to 2,4-diamino-1,3,5-triazinyl-6-phosphonic acid derivatives and their use in the preparation of self-extinguishing polymeric compositions based on thermoplastic polymers or polymers with elastomeric properties, especially olefinic polymers or copolymers, either alone or in combination with ammonium or amine phosphates and/or phosphonates.

2. Discussion of the Background

Various methods are known in the art for reducing or eliminating polymer combustibility. Some of these methods are based on the use of metal compounds, especially of antimony, bismuth or arsenic, in combination with partly halogenated thermally unstable organic compounds such as chlorinated paraffin waxes.

Other methods are based on the use of substances able to produce intumescence. Intumescent formulations generally consist of the polymer and at least three main additives, of which one is essentially phosphorated, its purpose being to form during combustion an impermeable semi-solid vitreous layer consisting essentially of polyphosphoric acid, and to activate the intumescence formation process, a second contains nitrogen for foaming purposes and the third contains carbon acting as a carbon donor for forming an insulating cellular layer (char) between the polymer and the flame.

Examples of intumescent formulations of this type are those described in the following patents: U.S. Pat. No. 3,810,862 (Phillips Petroleum Co.) based on melamine, pentaerythritol and ammonium polyphosphate, U.S. Pat. No. 4,727,102 (Vamp S.r.l.) based on melamine cyanurate, a hydroxyalkyl derivative of isocyanuric acid and ammonium polyphosphate, and published patent application WO 85/05626 (Plascoat U.K. Limited) based on various phosphorus and nitrogen compounds, and in particular a combination of melamine phosphate, pentaerythritol and ammonium polyphosphate.

In more recent formulations, in addition to the use of an organic or inorganic phosphorus compound, a nitrogen containing organic compound is used, generally an aminoplastic resin obtained by condensing urea, melamine or dicyandiamide with formaldehyde. Examples of formulations comprising two additives are described in U.S. Pat. No. 4,504,610 (Montedison S.p.A.) based on oligomeric derivatives of 1,3,5-triazine and ammonium polyphosphate, and European patent 14,463 (Montedison S.p.A.) based on organic compounds chosen from benzylguanamine and products of the reaction between aldehydes and various nitrogenated cyclic compounds, in particular benzylguanamine-formaldehyde copolymers, plus ammonium polyphosphate.

Self-extinguishing compositions can also be obtained by using single-component additives containing both nitrogen and phosphorus in the organic molecule, as described in U.S. Pat. No. 4,201,705 (Borg-Warner Corp.).

These intumescence retarding systems give the polymer containing them the property of forming a carbon residue following fire or the application of a flame. Retarding systems of this type have numerous advantages, including the absence of corrosion in the machines used to work the polymers, lower smoke emission than systems containing metal compounds and halogenated hydrocarbons, and in particular the possibility of achieving satisfactory flame retardant properties in the polymer with a smaller total quantity of additive and hence without excessive fall-off in the polymer mechanical properties.

SUMMARY OF THE INVENTION

The Applicant has now found that polymers can be given good flame retardant properties by using single component additives enabling polymeric compositions free of ammonium or amine phosphates or phosphonates to be obtained, or alternatively can be given excellent flame retardant properties if said additives are used in conjunction with a quantity of ammonium or amine phosphates and/or phosphonates which is much less than in the known art.

In terms of single component additives it is known in the art to use 2,4-diamino-1,3,5-triazinyl-6-phosphonic acid derivatives generally in the form of esters of N,N,N',N'-tetramethylol-2,4-diamino-1,3,5-triazinyl-6-phosphonic acid, as flame retardant additives in intumescent coatings for cellulose and its derivatives.

For example, U.S. Pat. Nos. 3,158,450, 3,165,513, 3,210,350, 3,650,670 and 3,654,274 refer to alkyl or alkenyl esters of 2,4-diamino-1,3,5-triazinyl-6-phosphonic acid carrying alkyl, aryl or methylol substituents on its amino groups, these being compounds able to confer flame retardant properties on wood, cotton and paper, but unable to confer self-extinguishing characteristics on thermoplastic polymers or polymers with elastomer properties, even in combination with ammonium or amine phosphates.

Even the use of diaminotriazinylphosphonic acid mono ester or of the free acid in association with the primary amino or methylolamino or alkylamino groups does not improve its properties as a flame retardant for thermoplastic polymers.

The insertion of a suitably chosen substituent, such as those indicated by the present Applicant, into the 2,4-diamino-1,3,5-triazinyl-6-phosphonic acid ester structure gives the additive such properties as to enable it to act as a flame retardant for the aforesaid polymers (provided its formulation includes ammonium or amine phosphates), however the thermal stability of the polymer compositions containing it is very low.

DETAILED DESCRIPTION OF THE PREFERRED EMBODIMENTS

The Applicant has now found that by using free 2,4-diamino-1,3,5-triazinyl-6-phosphonic acids carrying suitable substituents chosen from those described hereinafter, self-extinguishing polymeric compositions can be obtained having excellent thermal stability both towards thermal oxidation and during processing, without the need for further additives. This is still more advantageous in that the compositions can be worked at a higher temperature than in the known art.

The fact that the new additives have excellent stability under heat means that they maintain excellent flame retardant activity even following hot-working of the polymeric compositions which contain them.

Polymeric compositions containing the additives of the present invention also have the advantage of producing only very moderate, non obscuring smoke emission in the case of a fire.

The present invention therefore provides 2,4-diamino-1,3,5-triazinyl-6-phosphonic acid derivatives of general formula (I):

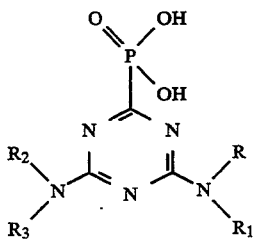

where:
at least one of the radicals from R to $R_3$ is:

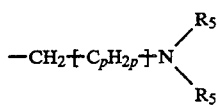

in which:
m is a whole number between 1 and 7, and preferably between 1 and 3;
p is a whole number between 1 and 5;
$R_4$ is H; $C_1$–$C_8$ alkyl, preferably H or $C_1$–$C_4$ alkyl; $C_2$–$C_6$ alkenyl; —[$C_qH_{2q}$]O—$R_6$ where q is a whole number between 1 and 4 and $R_6$ is H or $C_1$–$C_4$ alkyl; $C_6$–$C_{12}$ cycloalkyl or alkylcycloalkyl; provided that when $R_4$ is hydrogen, m is a whole number between 2 and 7, and preferably 2 or 3;
the radicals $R_5$, which can be the same or different, are: H; $C_1$–$C_8$ alkyl; $C_2$–$C_6$ alkenyl; $C_6$–$C_{12}$ cycloalkyl or alkylcycloalkyl; $C_1$–$C_4$ hydroxyalkyl; or the group:

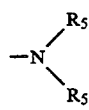

is replaced by a heterocyclic radical bound to the alkyl chain by the nitrogen atom and possibly containing a further heteroatom chosen preferably from O, S and N;
or in general formula (I) at least one of the groups:

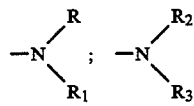

is replaced by a heterocyclic radical bound to the triazine ring by the nitrogen atom and possibly containing a further heteroatom chosen preferably from O, S and N.

The other radicals from R to $R_3$, which can be the same or different, have the aforesaid meaning or are H; $C_1$–$C_{18}$ alkyl; $C_2$–$C_8$ alkenyl; $C_6$–$C_{16}$ cycloalkyl or alkylcycloalkyl, possibly substituted with a hydroxyl or $C_1$–$C_4$ hydroxyalkyl function.

Examples of radicals from R to $R_3$ in general formula (I) are: methyl; ethyl; propyl; isopropyl; n-butyl; isobutyl; tert-butyl; n-pentyl; isopentyl; n-hexyl; tert-hexyl; octyl; tert-octyl; decyl; dodecyl; octadecyl; ethenyl; propenyl; butenyl; isobutenyl; hexenyl; octenyl; cyclohexyl; propylcyclohexyl; butylcyclohexyl; decylcyclohexyl; hydroxycyclohexyl; hydroxyethylcyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyethyl; 3-hydroxy-2,5-dimethylhexyl; 7-hydroxyheptyl; 7-hydroxyoctyl; 2-methoxyethl; 2-methoxypropyl; 3-methoxypropyl; 4-methoxybutyl; 6-methoxyethyl; 7-methoxyheptyl; 7-methoxyoctyl; 2-ethoxyethyl; 3-ethoxypropyl; 4-ethoxybutyl; 3-propoxypropyl; 3-butoxypropyl; 4-butoxybutyl; 4-isobutoxybutyl; 5-propoxypentyl; 2-cyclohexyloxyethyl; 2-ethenyloxyethyl; 2-(N,N-dimethylamino)ethyl; 3-((N,N-dimethylamino)propyl; 4-(N,N-dimethylamino)butyl; 5-(N,N-dimethylamino)pentyl; 4-(N,N-diethylamino)butyl; 5-(N,N-diethylamino)pentyl; 5-(N,N-diisopropylamino)pentyl; 3-(N-ethylamino)propyl; 4-(N-methylamino)butyl; 4-(N,N-dipropylamino)butyl; 2-(N,N-diisopropylamino)ethyl; 6-(N-hexenylamino)hexyl; 2-(N-ethenylamino)ethyl; 2-(N-cyclohexylamino)ethyl; 2-(N-2-hydroxyethylamino)ethyl; 2-(2-hydroxyethoxy)ethyl; 2-(2-methoxyethoxy)ethyl; 6-(N-propylamino)hexyl; and so forth.

Examples of heterocyclic radicals which can replace the groups:

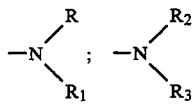

are:
aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine; and so forth.

Examples of heterocyclic radicals which can replace the group:

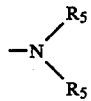

are:
aziridine; pyrrolidine; piperidine; morpholine; thiomorpholine; piperazine; 4-methylpiperazine; 4-ethylpiperazine; and so forth. Specific compounds included in formula (I) are given in the examples which follow this description.

The triazinylphosphonic acids of general formula (I) are prepared by hydrolyzing the corresponding ester derivatives of general formula (II):

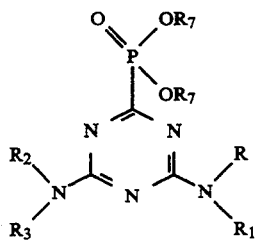 (II)

where the substituents from R to $R_3$ have the aforesaid meaning and the radicals $R_7$ are $C_1$-$C_4$ alkyl; $C_3$-$C_4$ alkenyl; phenyl; preferably $C_1$-$C_2$ alkyl.

The hydrolysis reaction is preferably conducted using the method described by T. Morita, Y. Okamoto and H. Sakurai, Bulletin of the Chemical Society of Japan 54, 267–273 (1981), which enables triazinylphosphonic acids to be obtained in good yield (exceeding 75%) under very mild conditions.

Compared with this method, it is not necessary to separate the products of general formula (I) in the form of aniline or cyclohexylamine salts, and the hydrolysis can also take place in water. The intermediate of general formula (II) is firstly reacted with trimethylchlorosilane and sodium or potassium iodide to give bis(trimethylsilyl) phosphonate of general formula (III):

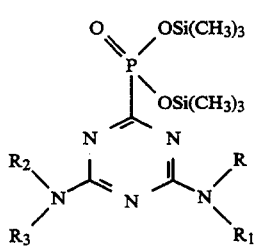 (III)

at a temperature of between 20° and 50° C. in acetonitrile, and then hydrolyzing the intermediate (III) with methyl alcohol or water at room temperature to give the phosphonic acids of general formula (I).

Good quality products are obtained generally in the form of white crystalline powder, which, as stated, do not need to be converted into the corresponding aniline or cyclohexylamine salts for separation.

The products of general formula (I) obtained in this manner can be used in self-extinguishing polymeric compositions without further purification.

The intermediates of general formula (II) can be synthesized by reacting a cyanuric halide, for example the chloride, at a temperature of between 0° and 200° C. in the presence or absence of a solvent (such as toluene, xylene etc.) with a phosphite of general formula (IV):

 (IV)

where $R_7$ has the aforesaid meaning, to give the intermediate of general formula (V):

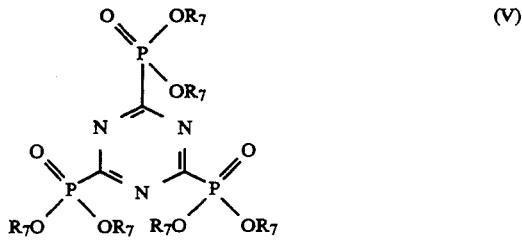 (V)

This intermediate, separated or not, is reacted at between 0° and 50° C. in a solvent (such as methyl alcohol, ethyl alcohol, xylene, dimethylsulphoxide, dimethylformamide, etc.) with an amine of general formula (IV):

 (VI)

where R and $R_1$ have the aforesaid meaning, to obtain the intermediate (VII):

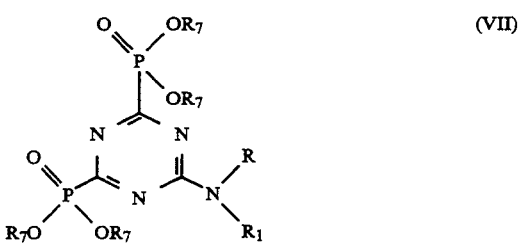 (VII)

This intermediate, separated or not, is then reacted under the aforesaid conditions with an amine of general formula (VII):

 (VIII)

where $R_2$ and $R_3$ have the aforesaid meaning, to obtain the intermediate (II)

An alternative method for obtaining the intermediates of general formula (II) is to change the order of addition of the various reagents, so that the cyanuric halide, for example the chloride, can be firstly reacted with the amine of general formula (VI) to give the intermediate of general formula (IX):

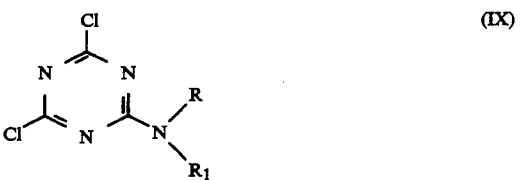 (IX)

and then with the amine of general formula (VIII) to give the intermediate of general formula (X):

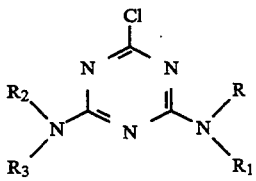

where the radicals from R to R₃ have the aforesaid meaning, and finally, with the phosphite of general formula (IV); or the intermediate of general formula (IX) can be reacted with the phosphite of general formula (IV) to give the intermediate of general formula (VII), then continuing as heretofore described.

The present invention also provides self-extinguishing polymeric compositions comprising:

a) from 90 to 40 parts by weight of a thermoplastic polymer or a polymer with elastomeric properties;
b) from 10 to 60, preferably from 15 to 45, parts by weight of one or more 2,4-diamino-1,3,5-triazinyl-6-phosphonic acid derivatives of general formula (I):

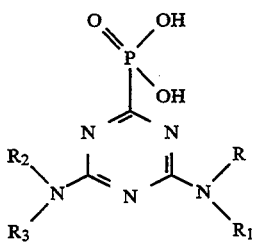

where the substituents from R to R₃ have the aforesaid meaning.

Particularly preferred are the compounds of general formula (I) in which one of the groups:

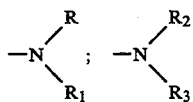

is replaced by an —NH₂ radical.

If it is desired to further increase the flame self-extinguishing properties of the polymeric compositions according to the present invention, from 1 to 25 parts by weight of one or more ammonium or amine phosphates and/or phosphonates can be added to them as replacement for a like number of parts by weight of component (b).

The preferred phosphates to be used in addition to component (b) are those ammonium polyphosphates of general formula $(NH_4)_{n+2}P_nO_{3n+1}$ in which n is a whole number equal to or greater than 2. Preferably the molecular weight of the polyphosphates is sufficiently high to ensure low water solubility. Indicatively, n varies preferably from 2 to 500.

The composition of the polyphosphates of the aforesaid formula, in which n is a sufficiently large number preferably between 50 and 500, is practically that which corresponds to the metaphosphate formula $(NH_4PO_3)_n$.

An example of these polyphosphates is that known by the commercial name of "Exolit 422" (produced and marketed by Hoechst) and having the composition $(NH_4PO_3)_n$ in which n is greater than 50. A further example is the product known by the name "Phos-Chek P/40" (Monsanto Chemicals) and having an analogous composition. A further polyphosphate which can be advantageously used, in particular because of its low water solubility, is that known by the commercial name of "Exolit 462" (produced and marketed by Hoechst) and corresponding to Exolit 422 microencapsulated in melamine-formaldehyde resin.

Other usable phosphates are those deriving from amines, such as dimethylammonium or diethylammonium phosphate, ethylenediamine phosphate, or melamine ortho or pyrophosphate.

Of the phosphonates, excellent results have been obtained using the ammonium phosphonates (mono or poly substituted) deriving from mono or polyphosphonic acids, examples of which are:

ethane-1,1,2-triphosphonic acid; 2-hydroxyethane-1,1,2-triphosphonic acid; propane-1,2,3-triphosphonic acid; methylphosphonic acid; ethylphosphonic acid; n-propylphosphonic acid; n-butylphosphonic acid; phenylphosphonic acid; 1-aminoethane-1,1-diphosphonic acid; 1-hydroxyethane-1,1-diphosphonic acid; 1-hydroxydodecane-1,1-diphosphonic acid; phosphonoacetic acid; 2-phosphonopropionic acid; 3-phosphonopropionic acid; 2-phosphonobutyric acid; 4-phosphonobutyric acid; aminotris(methylenephosphonic)acid; ethylenediaminetetra(methylenephosphonic)acid; hexamethylenediaminetetra(methylenephosphonic)acid; diethylenetriaminepenta(methylenephosphonic) acid; and so forth.

The preferred polymers usable in the compositions of the present invention are the polymers or copolymers of olefins of general formula R—CH=CH₂ where R is a hydrogen atom or a C₁-C₈ alkyl or aryl radical, and in particular:

1. isotactic or prevalently isotactic polypropylene;
2. HDPE, LLDPE or LDPE polyethylene;
3. crystalline copolymers of propylene with minor proportions of ethylene and/or other alpha-olefins, such as 1-butene, 1-hexene. 1-octene, or 4-methyl-1-pentene;
4. heterophasic compositions comprising A) a propylene homopolymeric fraction, or one of the copolymers of point 3, and B) a copolymeric fraction formed from elastomeric copolymers of ethylene with an alphaolefin, possibly containing minor proportions of a diene, the alpha-olefin being preferably chosen from propylene and 1-butene;
5. elastomeric copolymers of ethylene with alpha-olefins possibly containing minor proportions of a diene.

Examples of dienes most commonly present in said elastomer copolymers are butadiene, ethylidene-norbornene and 1,4-hexadiene. The preferred polymer of olefins of formula R—CH=CH₂ in which R is an aryl radical are high-impact and crystal polystyrene. Other examples of commonly used polymers are acrylonitrile/butadiene/styrene (ABS) and styrene/acrylonitrile (SAN) copolymers; polyurethane (polyester and polyether); polyethyleneterephthalate; polybutyleneterephthalate; polyamides; and so forth.

The self-extinguishing compositions of the present invention can be prepared by known methods, for example by firstly intimately mixing the ammonium or amine phosphate and/or phosphonate, if used, with one or more compounds of general formula (I) in finely ground form (preferably with particles less than 70 μm), then adding the mixture obtained to the polymer in a turbomixer to form a homogeneous mixture, which is extruded and granulated. The granulated product obtained in this manner can be transformed into various articles by any of the known moulding methods.

The flame retardant additives can also be used in fire retardant paints.

Triazinylphosphonic acids included in general formula (I) which are not cited in the examples but are equally advantageously usable in the self-extinguishing polymeric compositions of the present invention are shown in Table 1.

TABLE 1

| COMPOUND N° | R—N—R₁ | | R₂—N—R₃ | |
|---|---|---|---|---|
| 1 | ⟨N N—H⟩ | | H | H |
| 2 | CH₂CH₂CH₂OCH₃ | H | CH₂CH₂CH₂OCH₃ | H |
| 3 | ⟨N⟩ (piperidine) | | H | H |
| 4 | CH₂CH₂OH | H | ⟨cyclohexyl⟩ | H |
| 5 | ⟨N O⟩ (morpholine) | | t-C₄H₉ | H |
| 6 | CH₂CH₂OH | H | CH₂—CH=CH₂ | H |
| 7 | ⟨N S⟩ (thiomorpholine) | | t-C₂H₁₇ | H |
| 8 | (CH₂)₃OH | H | (CH₂)₃OH | H |
| 9 | ⟨(CH₂)₃N O⟩ | H | H | H |
| 10 | ⟨N S⟩ | | CH₂CH₂OCH₃ | H |
| 11 | ⟨N ⟩ (pyrrolidine) | | H | H |
| 12 | CH₂CHOH\|CH₃ | H | CH₂CHOH\|CH₃ | H |
| 13 | (CH₂)N(C₂H₅)₂ | H | H | H |
| 14 | (CH₂)₄OCH₃ | H | H | H |
| 15 | (CH₂)₂O(CH₂)₂OH | H | H | H |
| 16 | (CH₂)₃OC₂H₅ | H | H | H |
| 17 | ⟨N O⟩ (morpholine) | | CH₂—CH=CH₂ | H |
| 18 | (CH₂)₅OH | H | H | H |
| 19 | CH₂CH₂OCH=CH₂ | H | H | H |

The structures of the compounds of general formula (I) described in the examples were confirmed by NMR analysis.

The following examples illustrate but do not limit the characteristics of the invention.

EXAMPLE 1

184.5 g of cyanuric chloride and 1 liter of toluene are fed into a 3 liter reactor fitted with a stirrer thermometer, dropping funnel, reflux condenser and heating bath.

The dispersion is stirred at room temperature, after which 498.5 g of triethylphosphite are fed in over about 4 hours.

The reaction is initially exothermic and the temperature reaches 45° C.; the value of 45° C. is then maintained by heating the mass externally.

When all the reagent has been added the mixture is heated to 70° C. and maintained under stirring at this temperature for about 6 hours, until ethyl chloride development ceases. A homogeneous solution is obtained.

The solvent is then distilled off, and the distillation residue after cooling to room temperature is taken up in 300 cm³ of n-hexane.

The product which forms is filtered off and washed on the filter with n-hexane.

On drying the filter cake in an oven under vacuum at 70° C. 463.1 g of the intermediate (XI):

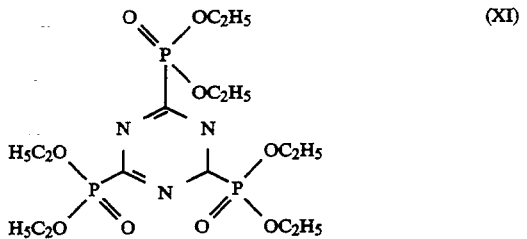

are obtained as a crystalline product with m.p.=91°–94° C. (m.p.=melting point) and with a phosphorus content of 19.38% (theoretical=19.02%).

700 cm³ of ethyl alcohol, 146.7 g of the intermediate (XI) and, under agitation, 26.1 g of morpholine are fed into a 2 liter reactor equipped as the preceding.

The mixture is stirred at room temperature for 3 hours. The solvent is then distilled off and the oily distillation residue taken up in 500 cm³ of a 1:4 n-hexane/ethyl ether mixture. The product which separates is filtered off and washed on the filter with the same mixture.

On drying under vacuum, 126.9 g of the intermediate (XII):

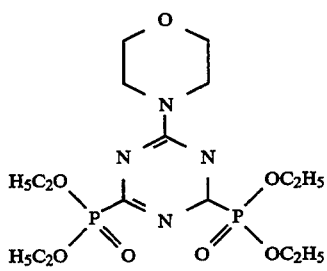 (XII)

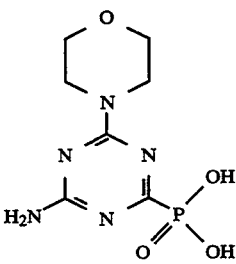 (XIII)

are obtained as a crystalline product with m.p.=73°–75° C. and with a phosphorus content of 13.82% (theoretical=14.15%). 800 cm$^3$ of anhydrous ethyl alcohol and 109.5 g of the intermediate (XII) are fed into the same 2 liter reactor, but fitted with a cooling bath.

Stirring is applied until a solution is obtained, after which it is cooled externally to 0°–3° C. and the solution saturated with gaseous ammonia.

The temperature is allowed to rise to 10°–15° C. and stirring maintained for about 24 hours.

At the end of the reaction the solvent is distilled off, and the distillation residue in the form of a very dense oil is taken up in 400 cm$^3$ of a 1:1 n-hexane/ethyl ether mixture. The product which separates is filtered off and washed on the filter with the same mixture.

On drying in an oven under vacuum, 76.7 g of the intermediate (XIII):

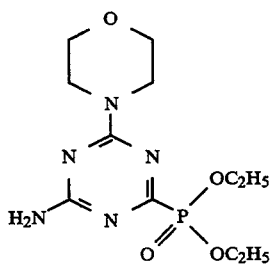 (XIII)

are obtained as a white crystalline product with m.p.=96°–100° C. and with a phosphorus content of 9.49% (theoretical=9.78%). The structure of the intermediates (XI), (XII) and (XIII) was confirmed by NMR analysis.

300 cm$^3$ of acetonitrile, 63.4 g of the intermediate (XIII) and 60.0 g of sodium iodide are fed into a 1 liter reactor equipped as the preceding.

The mixture is heated to 35° C., and while maintaining this temperature 43.4 g of trimethylchlorosilane are fed in over 30 minutes. The mixture is maintained under stirring at 35° C. for 2 hours, after which the reaction mass is filtered to eliminate the sodium chloride formed, the residue being washed on the filter with two 100 cm$^3$ portions of ethyl ether.

The solvent is distilled off under reduced pressure at a temperature of less than 50° C. and the distillation residue is treated with 200 cm$^3$ of methyl alcohol at room temperature. The product formed is separated by filtration and washed on the filter with methyl alcohol.

On drying the filter cake in an oven, 44.1 g of the product:

are obtained as a white crystalline powder with m.p. exceeding 300° C. and with a phosphorus content of 11.37% (theoretical=11.88%).

EXAMPLE 2

800 cm$^3$ of toluene and 110.7 g of cyanuric chloride are fed into the 2 liter reactor of Example 1.

The dispersion is heated to 80° C., and 224 g of trimethylphosphite are fed in over about 2 hours. There is an immediate development of methyl chloride. The mass is maintained under stirring for a further hour at 80° C., after which it is heated to boiling and maintained under reflux for about 1 hour, until the development of methyl chloride ceases. A homogeneous solution is obtained. It is allowed to cool to room temperature. A precipitate forms as white crystals. The mass is further cooled to 5° C., the product filtered off and washed on the filter firstly with xylene and then with n-hexane.

On drying the filter cake in an oven under vacuum at 70° C., 233.8 g of the intermediate (XIV):

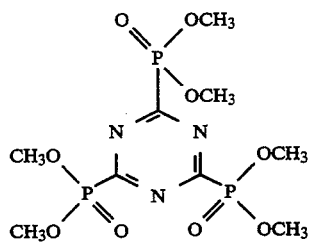 (XIV)

are obtained as a white crystalline powder with m.p.=119°–122° C. and with a phosphorus content of 22.77% (theoretical=22.96%). 750 cm$^3$ of anhydrous ethyl alcohol, 121.5 g of the intermediate (XIV) and 22.5 g of 2-methoxyethylamine are fed into the same 2 liter reactor, but fitted with a cooling bath.

The mass is left under stirring at room temperature for about 4 hours, after which the solution is cooled to 0°–3° C. and saturated with gaseous ammonia.

The temperature is allowed to rise to about 10° C. and stirring maintained for about 20 hours at this temperature.

At the end of the reaction the solvent is distilled off, and the distillation residue in the form of an oil is taken up in 500 cm$^3$ of a 1:1 n-hexane/ethyl ether mixture.

The product which separates is filtered off and washed on the filter with the same mixture.

On drying under vacuum at ambient temperature, 74.2 g of the intermediate (XV):

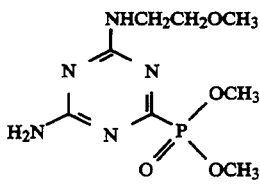

are obtained as a crystalline product with m.p.=45°–49° C. and with a phosphorus content of 10.82% (theoretical=11.19%).

The structure of the intermediates (XIV) and (XV) was confirmed by NMR analysis.

300 cm³ of acetonitrile, 55.4 g of the intermediate (XV) and 66.4 g of potassium iodide are fed into the 1 liter apparatus of Example 1.

The mixture is heated to 30° C., and while maintaining this temperature 43.4 g of trimethylchlorosilane are fed in over 40 minutes.

The mixture is maintained under stirring at 30° C. for a further hour, after which the reaction mass is filtered to eliminate the potassium chloride formed, the residue being washed on the filter with two 100 cm³ portions of ethyl ether.

The solvent is distilled off under reduced pressure at a temperature of less than 50° C. and the distillation residue is treated with 200 cm³ of methyl alcohol at room temperature. Proceeding as described in Example 1, 38.5 g of the product:

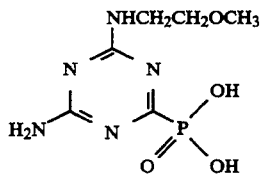

are obtained as a white crystalline powder with m.p.=218°–223° C. and with a phosphorus content of 11.94% (theoretical=12.45%).

EXAMPLE 3

184.5 g of cyanuric chloride and 1300 cm³ of methylene chloride are fed into the 3 liter apparatus described in Example 1 but provided initially with a cooling bath.

After cooling from the outside, 87.2 g of morpholine and 40 g of sodium hydroxide dissolved in 150 cm³ of water are fed in simultaneously over 3 hours while maintaining the pH between 5 and 7 and the temperature between 0° and 3° C.

The temperature is maintained at 0°–3° C. for a further 3 hours, after which the aqueous phase is separated.

By distilling off the methylene chloride 230 g of the intermediate (XVI):

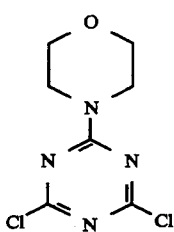

are obtained in the form of a white crystalline powder with m.p.=155°–157° C., at a purity exceeding 98% (determined by gas chromatography) and with a chlorine content of 29.87% (theoretical=30.21%).

700 cm³ of xylene and 141.0 g of the intermediate (XVI) are fed into the 2 liter apparatus of the preceding examples.

The mixture is heated to about 100° C., after which 199.2 g of triethylphosphite are fed in over a time of 3 hours. The temperature is then raised to 115° C. and maintained for 12 hours, until ethyl chloride development ceases.

At the end of the reaction, the solution is concentrated by distilling off about 400 cm³ of solvent, after which the product formed is precipitated by adding to the distillation residue 800 cm³ of a 4:1 n-hexane/ethyl ether mixture.

The product which separates is filtered off and washed on the filter with the same mixture.

On drying the filter cake in an oven under vacuum 226.7 g of the intermediate (XII) are obtained, with a phosphorus content of 13.76% (theoretical=14.15%).

300 cm³ of dimethylsulphoxide, 109.5 g of the intermediate (XII) and 20.6 g of 2-methoxyethylamine are fed into a 1 liter reactor equipped as the preceding.

The solution is maintained under stirring at room temperature for about 32 hours, after which the product formed is precipitated by adding the reaction solution to 800 cm³ of a water/ice mixture.

The product is filtered off and dried in an oven under vacuum at 50° C.

74.1 g of the intermediate (XVII):

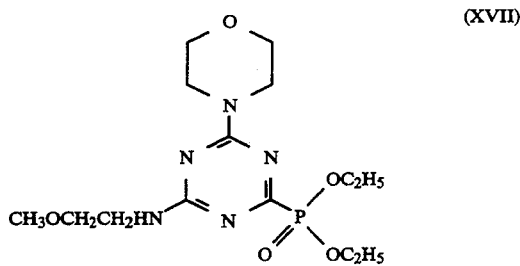

are obtained as a crystalline product with m.p.=93°–95° C. and with a phosphorus content of 8.25% (theoretical=8.27%).

The structure of the intermediate (XVII) was confirmed by NMR analysis.

300 cm³ of acetonitrile, 75.0 g of the intermediate (XVII) and 60.0 g of sodium iodide are fed into the same 1 liter reactor.

The mixture is heated to 35° C., and while maintaining this temperature 43.4 g of trimethylchlorosilane are fed in over a time of 1 hour.

The mixture is maintained under stirring at 35° C. for 2 hours, after which the procedure described in the preceding examples is exactly followed.

51.5 g of the product:

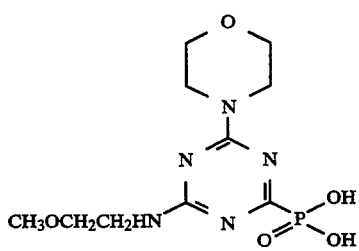

are obtained as a white crystalline powder with m.p. exceeding 300° C. and with a phosphorus content of 9.58% (theoretical=9.72%).

EXAMPLE 4

184.4 g of cyanuric chloride and 800 cm³ of methylene chloride are fed into a 2 liter reactor equipped as in the preceding examples. 174 g of morpholine dissolved in 150 cm³ of water are added over a period of 2 hours to the solution, which is maintained at 4°-5° C. by cooling from the outside.

The temperature is allowed to rise to 10° C., and while maintaining it between 10° and 20° C. a solution of 80 g of sodium hydroxide in 200 cm³ of water is added over 4 hours. The temperature of 20° C. is maintained for a further 2 hours, after which the aqueous phase is eliminated.

On distilling the methylene chloride 270 g of the intermediate (XVIII):

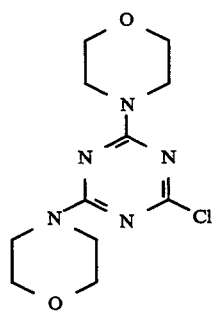

(XVIII)

are obtained as a white crystalline powder with m.p.=172°-174° C. and with a chlorine content of 12.31% (theoretical=12.43%). 166 g of triethylphosphite and 114.2 g of the intermediate (XVIII) are fed into a 0.5 liter reactor equipped as the preceding.

The mixture is heated to boiling and maintained under reflux for about 16 hours, until ethyl chloride development ceases.

The excess triethylphosphite is then eliminated by distillation at 70 mmHg and the distillation residue is treated with 500 cm³ of a 1:2 acetone/n-hexane mixture.

The product which forms is separated by filtration and washed on the filter with the same mixture.

On drying the filter cake in an oven under vacuum at 70° C., 128.6 g of the intermediate (XIX):

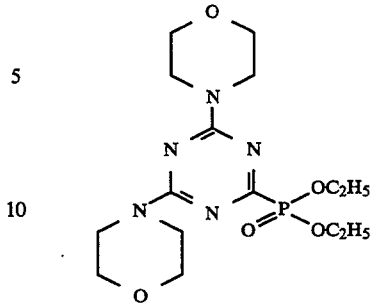

(XIX)

are obtained as a white crystalline product with m.p.=121°-122° C. and with a phosphorus content of 7.96% (theoretical=8.01%).

The structure of the intermediates (XVIII) and (XIX) was confirmed by NMR analysis.

300 cm³ of acetonitrile, 77.4 g of the intermediate (XIX) and 60.0 g of sodium iodide are fed into the 1 liter reactor of Example 1.

The mixture is heated to 40° C., and while maintaining this temperature 43.4 g of trimethylchlorosilane are fed in over 30 minutes.

The mixture is maintained under starring at 40° C. for a further 1 hour and 30 minutes, after which the reaction mass is filtered to remove the formed sodium chloride, the residue being washed on the filter with 100 cm³ of ethyl ether.

The solvent is distilled off at 40° C. under reduced pressure and the distillation residue is treated with 200 cm³ of methyl alcohol.

The procedure described in the preceding examples is then followed and 54.6 g of the product:

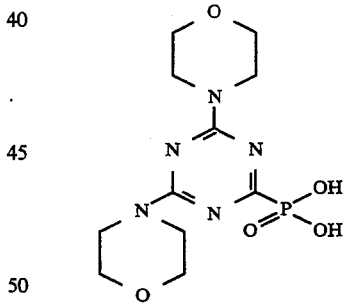

are obtained as a white crystalline powder with m.p. =exceeding 300° C. and with a phosphorus content of 9.18% (theoretical=9.36%).

EXAMPLES 5-9

Operating under conditions analogous to those described in Examples 1 to 4, the products of general formula (I) shown in Table 2 with m.p. exceeding 300° C. are prepared.

TABLE 2

| EXAMPLE N°. | R—N—R$_1$ | | R$_2$—N—R$_3$ | | % phosphorus calculated | found |
|---|---|---|---|---|---|---|
| 5 | CH$_2$CH$_2$OH | H | H | H | 13,19 | 12,88 |

TABLE 2-continued

| EXAMPLE N°. | R—N—R$_1$ | R$_2$—N—R$_3$ | % phosphorus calculated | found |
|---|---|---|---|---|
| 6 | ⌬N S (piperidine-like with S) | H H | 11,19 | 11,06 |
| 7 | ⌬N O (morpholine) | CH$_2$CH$_2$OH  H | 10,16 | 9,97 |
| 8 | ⌬N N—CH$_3$ (piperazine-N-methyl) | H H | 11,31 | 11,20 |

Table 3

Table 3 shows the results of thermogravimetric analysis (T.G.A.) of some triazinylphosphonic acids of general formula (I) described in the examples of the present invention, compared with those of the corresponding esters of general formula (II).

The thermal stability of these products was determined by evaluating the weight lost on temperature increase.

A DU PONT Model 951-9900 thermobalance was used, operating with an air rate of 5 liters/hour, a heating rate of 20° C./minute within the temperature range of 20°–600° C., and a product quantity of about 10 mg.

TABLE 3

| Weight loss (%) | Temperature at which weight loss occurs |||| | |
| | Product Example 1 || Product Example 3 || Product Example 4 ||
| | (I) | (II) | (I) | (II) | (I) | (II) |
|---|---|---|---|---|---|---|
| 2 | 264 | 246 | 287 | 255 | 282 | 250 |
| 5 | 276 | 263 | 298 | 270 | 295 | 265 |
| 10 | 295 | 275 | 314 | 283 | 307 | 278 |
| 20 | 306 | 287 | 326 | 297 | 319 | 295 |
| 50 | 416 | 334 | 421 | 321 | 412 | 344 |

(I) - Triazinylphosphonic acids of general formula (I)
(II) - Corresponding esters of general formula (II).

Tables 4 and 5

The tests indicated in Tables 4 and 5 relate to polymeric compositions containing the products of general formula (I) prepared as in the preceding examples.

Test pieces in the form of plates of about 3 mm thickness were prepared by moulding mixtures of granular polymer and additives in a MOORE plate press, operating for 7 minutes at a pressure of 40 kg/cm$^3$.

The self-extinguishing level was determined on the plates obtained in this manner by measuring the oxygen index (L.O.I. in accordance with ASTM D-2863/77) in a Stanton Redcroft apparatus, and applying the Vertical Burning Test which makes it possible the material to be classified in three classes, namely 94 V-0, 94 V-1 and 94 V-2 in accordance with the UL 94 standards (published by the "Underwriters Laboratories" USA).

Table 4 shows the values obtained using an isotactic polypropylene in flake form with a melt flow index of 12 and with 96 wt % insoluble in boiling n-heptane.

Table 5 shows the values obtained using a low density polyethylene in granular form with a melt flow index of 7; a polystyrene in granular form containing 5 wt % of butadiene rubber and with a melt flow index of 9; a polyester thermoplastic polyurethane (ESTANE 54600 ® by Goodrich) and a polyether thermoplastic polyurethane (ESTANE 58300 ® by Goodrich) in granular form of density 1.19 and 1.10 g/cm$_3$ respectively; an ethylene-propylene elastomer copolymer containing 45 wt % of polypropylene; and an acrylonitrile-butadiene-styrene terpolymer with a density of 1.06 and a melt flow index of 1.6 and containing about 40% of acrylonitrile and styrene and 20% of butadiene.

TABLE 4

| Example N° | Product Example | Parts by weight |||| L.O.I. (ASTM D2863) | UL94 (3 mm) |
| | | Product | PP$_{(1)}$ | AO$_{(2)}$ | APP$_{(1)}$ | | |
|---|---|---|---|---|---|---|---|
| 9 | 1 | 34,0 | 65 | 1 | 0 | 35,0 | V0 |
| 10 | 1 | 12,0 | 75 | 1 | 12,0 | 36,2 | V0 |
| 11 | 1 | 17,0 | 65 | 1 | 17,0 | 44,1 | V0 |
| 12 | 2 | 34,0 | 65 | 1 | 0 | 31,9 | V0 |
| 13 | 2 | 16,0 | 75 | 1 | 8,0 | 30,6 | V0 |
| 14 | 3 | 29,0 | 70 | 1 | 0 | 32,7 | V0 |
| 15 | 4 | 12,0 | 75 | 1 | 12,0 | 37,4 | V0 |
| 16 | 5 | 30,0 | 69 | 1 | 0 | 32,2 | V0 |
| 17 | 6 | 34,0 | 65 | 1 | 0 | 35,7 | V0 |
| 18 | 6 | 22,7 | 65 | 1 | 11,3 | 40,6 | V0 |
| 19 | 7 | 29,0 | 70 | 1 | 0 | 33,3 | V0 |
| 20 | 7 | 16,0 | 75 | 1 | 8,0 | 34,1 | V0 |
| 21 | 8 | 34,0 | 65 | 1 | 0 | 34,0 | V0 |
| 22 | 1 | 27,2 | 65 | 1 | 6,8* | 39,5 | V0 |
| 23 | 5 | 16,0 | 75 | 1 | 8,0* | 33,2 | V0 |

TABLE 4-continued

| Example N° | Product Example | Parts by weight | | | | L.O.I. (ASTM D2863) | UL94 (3 mm) |
|---|---|---|---|---|---|---|---|
| | | Product | $PP_{(1)}$ | $AO_{(2)}$ | $APP_{(1)}$ | | |
| 24 | 8 | 19,5 | 73 | 1 | 6,5[3] | 34,8 | V0 |

PP = polypropylene
APP = ammonium polyphosphate - Exolit 4220 TM (Hoechst)
* = APP microencapsulated with melamine-formaldehyde resin Exolit 462 TM (Hoechst)
(2) AO = antioxidant
Mixture consisting of 2 parts of dilaurylthiopropionate and 1 part of pentaerythritol tetra[3-(3,5-di-tert-butyl-4-hydroxyphenyl)propionate]
(3) APP replaced with the monoammonium salt of 1-aminoethane-1,1-diphosphonic acid

TABLE 5

| Example N° | Polymeric support(1) | Product Example N° | Parts by weight | | | | L.O.I. (ASTM D2863) | UL 94 (3 mm) |
|---|---|---|---|---|---|---|---|---|
| | | | Product | Polymer | $AO^{(2)}$ | $APP^{(1)}$ | | |
| 25 | LDPE | 1 | 17,0 | 65 | 1 | 17,0 | 33,7 | V0 |
| 26 | | 7 | 26,0 | 60 | 1 | 13,0 | 35,8 | V0 |
| 27 | HIPS | 6 | 19,5 | 60 | 1 | 19,5 | 37,0 | V0 |
| 28 | | 7 | 19,5 | 60 | 1 | 19,5 | 34,6 | V0 |
| 29 | PU | 1 | 29,0 | 70 | 1 | 0 | 33,8 | V0 |
| 30 | ester | 6 | 29,0 | 70 | 1 | 0 | 34,8 | V0 |
| 31 | | 8 | 29,0 | 70 | 1 | 0 | 34,4 | V0 |
| 32 | PU ether | 8 | 29,0 | 70 | 1 | 0 | 30,7 | V0 |
| 33 | PP/PE | 1 | 39,0 | 60 | 1 | 0 | 32,2 | V0 |
| 34 | | 2 | 19,3 | 70 | 1 | 9,7 | 32,8 | V0 |
| 35 | ABS | 6 | 17,0 | 65 | 1 | 17,0 | 32,1 | V0 |

(1) APP = ammonium polyphosphate - Exolit 422 TM (Hoechst)
LPDE = low density polyethylene
HIPS = polystyrene containing 5% of butadiene rubber
PU (ester) = polyurethane polyester
PU (ether) = polyurethane polyester
PP/PE = propylene-ethylene copolymer
ABS = acrylonitrile-butadiene-styrene terpolymer
(2) AO = antioxidant
Mixture consisting of 2 parts of dilaurylthiopropionate and 1 part of pentaerythritol tetra 3-(3,5-di-tert-butyl-4-hydroxyphenyl)prionate

EXAMPLE 36 (comparison)

600 cm³ of anhydrous ethyl alcohol and 146.7 g of the intermediate (XI) are fed into a 1 liter reactor equipped as in Example 1. The solution is cooled to 0°-2° C. from the outside and then saturated with gaseous ammonia, maintaining the temperature between 5° and 10° C.

The solution is left standing at about 15° C. for about 40 hours. The product which forms is separated by filtration and washed on the filter firstly with water and then with acetone.

On drying the filter cake in an oven at 80° C., 63.1 g of the intermediate (XX):

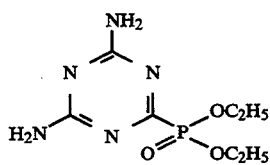

are obtained as a white crystalline powder with m.p.=271°-273° C. (with decomposition) and with a phosphorus content of 12.44% (theoretical=12.55%).

350 cm³ of acetonitrile, 49.4 g of the intermediate (XX) and 60.0 g of sodium iodide are fed into the same 1 liter reactor. The mixture is heated to 45° C., and while maintaining this temperature 43.4 g of trimethylchlorosilane are fed in over a time of 45 minutes.

The mixture is maintained under stirring at 45° C. for a further 4 hours, after which the procedure described in Examples 1 to 4 is followed.

29.2 g of the 2,4-diamino-1,3,5-triazinyl-6-phosphonic acid (XXI):

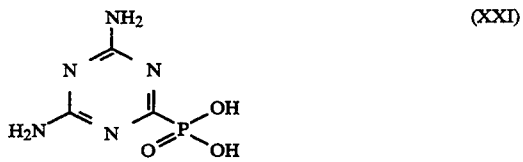

are obtained as a white crystalline powder with m.p. exceeding 300° C. and with a phosphorus content of 15.92% (theoretical=16.23%).

Operating in accordance with the method used in Examples 9 to 24 and using the product (XXI), the following composition was prepared:

| Polypropylene | 65 parts by weight |
|---|---|
| Antioxidant | 1 part by weight |
| Product (XXI) | 34 parts by weight |

Using this composition, test pieces were prepared and subjected to self-extinguishing tests in the aforedescribed manner.

The following results were obtained:
L.O.I.=25.3
UL 94 (3 mm): class B (the test piece burns)

EXAMPLE 37 (comparison)

Operating in the manner of Example 36, the following composition is prepared:

| Polypropylene | 73 parts by weight |
| --- | --- |
| Antioxidant | 1 part by weight |
| Ammonium polyphosphate | 13 parts by weight |
| Product (XXI) | 13 parts by weight |

Using this composition, test pieces were prepared and subjected to self-extinguishing tests in the aforedescribed manner.

The following results were obtained:
L.O.I.=26.1
UL 94 (3 mm): class B (the test piece burns)

We claim:

1. A self-extinguishing polymeric composition comprising:
   (a) from 90 to 40 parts by weight of a thermoplastic polymer or a polymer with elastomeric properties; and
   (b) from 10 to 60 parts by weight of one or more 2,4-diamino-1,3,5-triazinyl-6-phosphonic acid derivatives of the formula (I):

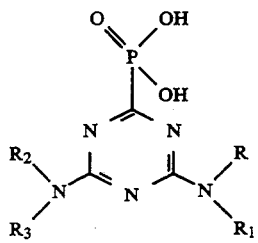

(I)

wherein at least one of the radicals R, $R_1$, $R_2$ and $R_3$ is selected from the group consisting of $-CH_2+C_mH_{2m}+O-R_4$ and

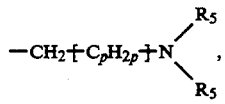

in which:
   m is a whole number between 1 and 7;
   p is a whole number between 1 and 5;
   $R_4$ is selected from the group consisting of H; $C_1-C_8$ alkyl; $C_2-C_6$ alkenyl; $C_6-C_{12}$ cycloalkyl; $C_1-C_8$-alkyl-$C_6-C_{12}$-cycloalkyl; and $-C_qH_{2q}-O-R_6$, where q is a whole number between 1 and 4 and $R_6$ is H or $C_1-C_4$ alkyl; provided that when $R_4$ is H, m is a whole number between 2 and 7; and
   the radicals $R_5$, which can be the same or different, are selected from the group consisting of H; $C_1-C_8$ alkyl; $C_2-C_6$ alkenyl; $C_6-C_{12}$ cycloalkyl; $C_1-C_8$-alkyl-$C_6-C_{12}$-cycloalkyl; and $C_1-C_4$ hydroxyalkyl; or
   one or more pairs of radicals selected from the group consisting of (a) R and $R_1$, (b) $R_2$ and $R_3$, and (c) the radicals $R_5$ may be joined to form a heterocyclic radical selected from the group consisting of aziridine, pyrrolidine, piperidine, morpholine, thiomorpholine and piperazine, each of which may be substituted with from 1 to 4 $C_1-C_2$ alkyl groups, and
   the remaining radicals R, $R_1$, $R_2$ and $R_3$, which can be the same or different, are selected from the group consisting of H; $C_1-C_8$ alkyl; $C_2-C_8$ alkenyl; $C_6-C_{16}$ cycloalkyl; and $C_1-C_8$-alkyl-$C_6-C_{12}$- cycloalkyl, each of which may be substituted with a hydroxyl or $C_1-C_4$ hydroxyalkyl group.

2. The self-extinguishing polymeric composition of claim 1, wherein $R_2$ and $R_3$ are joined to form a heterocyclic radical selected from the group consisting of aziridine, pyrrolidine, piperidine, morpholine, thiomorpholine and piperazine, each of which may be substituted with from 1 to 4 $C_1-C_2$ alkyl groups.

3. The self-extinguishing polymeric composition of claim 1, where R is selected from the group consisting of

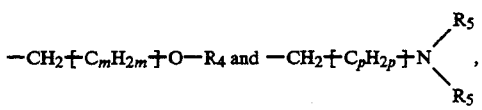

in which:
   m is a whole number between 1 and 7;
   p is a whole number between 1 and 5;
   $R_4$ is selected from the group consisting of H; $C_1-C_8$ alkyl; $C_2-C_6$ alkenyl; $-C_qH_{2q}-O-R_6$, where q is a whole number between 1 and 4 and $R_6$ is H or $C_1-C_4$ alkyl; $C_6-C_{12}$ cycloalkyl and $C_1-C_8$-alkyl-$C_6-C_{12}$-cycloalkyl; provided that when $R_4$ is H, m is a whole number between 2 and 7; and
   the radicals $R_5$, which can be the same or different, are selected from the group consisting of H; $C_1-C_8$ alkyl; $C_2-C_6$ alkenyl; $C_6-C_{12}$ cycloalkyl; $C_1-C_8$-alkyl-$C_6-C_{12}$-cycloalkyl; and $C_1-C_4$ hydroxyalkyl; and
   $R_1$, $R_2$ and $R_3$ are each H.

4. The self-extinguishing polymeric composition of claim 1, wherein R, $R_1$, $R_2$ and $R_3$ are said pairs of radicals (a) and (b), and each of said pairs is joined to form said heterocyclic radical.

5. The self-extinguishing polymeric composition of claim 1, wherein at least one of R, $R_1$, $R_2$ and $R_3$ is $-CH_2-C_mH_{2m}-O-R_4$, in which m is from 1 to 3 and $R_4$ is hydrogen or $C_1-C_4$-alkyl, provided that when $R_4$ is hydrogen, m is 2 or 3.

6. The self-extinguishing polymeric composition of claim 1, wherein the group $-N(R_5)_2$ is a heterocyclic radical selected from the group consisting of aziridine, pyrrolidine, piperidine, morpholine, thiomorpholine, piperazine, 4-methylpiperazine and 4-ethylpiperazine.

7. The self-extinguishing polymeric composition of claim 1, wherein one of said pairs of radicals selected from the group consisting of (a) R and $R_1$ and (b) $R_2$ and $R_3$ are each H.

8. A self-extinguishing polymeric composition comprising:
   (a) from 90 to 40 parts by weight of a thermoplastic polymer or a polymer with elastomeric properties; and
   (b) from 9 to 35 parts by weight of one or more 2,4-diamino-1,3,5-triazinyl-6-phosphonic acid derivatives of the formula (I):

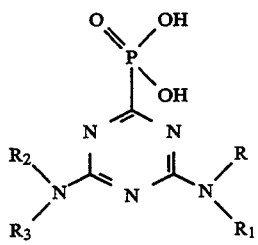 (I)

wherein at least one of the radicals R, $R_1$, $R_2$ and $R_3$ is selected from the group consisting of —$CH_2$ $C_mH_{2m}$ O—$R_4$ and

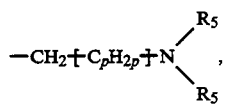

in which:

m is a whole number between 1 and 7;
p is a whole number between 1 and 5;
$R_4$ is selected from the group consisting of H; $C_1$–$C_8$ alkyl; $C_2$–$C_6$ alkenyl; $C_6$–$C_{12}$ cycloalkyl; $C_1$–$C_8$-alkyl-$C_6$–$C_{12}$-cycloalkyl; and $C_qH_{2q}$ O—$R_6$, where q is a whole number between 1 and 4 and $R_6$ is H or $C_1$–$C_4$ alkyl; provided that when $R_4$ is H, m is a whole number between 2 and 7; and
the radicals $R_5$, which can be the same or different, are selected from the group consisting of H; $C_1$–$C_8$ alkyl; $C_2$–$C_6$ alkenyl; $C_6$–$C_{12}$ cycloalkyl; $C_1$–$C_8$-alkyl-$C_6$–$C_{12}$-cycloalkyl; and $C_1$–$C_4$ hydroxyalkyl; or
one or more pairs of radicals selected from the group consisting of (a) R and $R_1$, (b) $R_2$ and $R_3$, and (c) the radicals $R_5$ may be joined to form a heterocyclic radical selected from the group consisting of aziridine, pyrrolidine, piperidine, morpholine, thiomorpholine and piperazine, each of which may be substituted with from 1 to 4 $C_1$–$C_2$ alkyl groups, and
the remaining radicals R, $R_1$, $R_2$ and $R_3$, which can be the same or different, are selected from the group consisting of H; $C_1$–$C_8$ alkyl; $C_2$–$C_8$ alkenyl; $C_6$–$C_{16}$ cycloalkyl; and $C_1$–$C_8$-alkyl-$C_6$–$C_{12}$-cycloalkyl, each of which may be substituted with a hydroxyl or $C_1$–$C_4$ hydroxyalkyl group, and
(c) from 1 to 25 parts by weight of one or more ammonium phosphates, amine phosphates, ammonium phosphonates, amine phosphonates or mixtures thereof.

9. The self-extinguishing polymeric composition of claim 8, wherein said component (c) is of the formula $(NH_4)_{n+2}P_nO_{3n+1}$, where n is a whole number equal to or greater than 2.

10. The self-extinguishing polymeric composition of claim 8, wherein said component (c) is of the formula $(NH_4PO_3)_n$, wherein n is a whole number between 50 and 500.

11. The self-extinguishing polymeric composition of claim 8, wherein said component (c) is selected from the group consisting of dimethylammonium phosphate, diethylammonium phosphate, ethylenediamine phosphate, melamine orthophosphate and melamine pyrophosphate.

12. The self-extinguishing polymeric composition of claim 1 or 8, wherein the polymer (a) is selected from the group consisting of polymers and copolymers of olefins of the formula R—CH=$CH_2$, where R is a hydrogen atom or a $C_1$–$C_8$ alkyl or aryl radical; acrylonitrile/butadiene/styrene terpolymers; styrene/acrylonitrile copolymers; polyurethanes; polyethylene terephthalate; polybutylene terephthalate and polyamides.

13. The self-extinguishing polymeric composition of claim 12, wherein the polymer (a) is selected from the group consisting of:
  (a) isotactic or prevalently isotactic polypropylene;
  (b) HDPE, LLDPE or LDPE polyethylene;
  (c) crystalline copolymers of propylene with minor proportions of ethylene, 1-butene, 1-hexane, 1-octene, 4-methyl-1-pentene or a mixture thereof;
  (d) heterophasic compositions comprising
    (A) a propylene homopolymeric fraction or a crystalline copolymer of propylene with a minor proportion of ethylene, 1-butene, 1-hexane, 1-octene, 4-methyl-1-pentene or a mixture thereof, and
    (B) a copolymeric fraction formed from elastomeric copolymers of ethylene with an alpha-olefin, which may contain a minor proportion of a diene; and
  (e) elastomeric copolymers of ethylene with one or more alpha-olefins, which may contain a minor proportion of a diene.

14. The self-extinguishing polymeric composition of claim 13, wherein the polymer (a) is said elastomeric copolymer (e), and said alpha-olefin is propylene, 1-butene or a mixture thereof.

15. An article obtained by moulding the self-extinguishing polymeric composition of claim 1 or 8.

* * * * *